United States Patent [19]

Finger

[11] Patent Number: Plant 5,894

[45] Date of Patent: Mar. 3, 1987

[54] KALANCHOE PLANT NAMED SATISFACTION

[75] Inventor: Hermann Finger, Wiesmoor, Fed. Rep. of Germany

[73] Assignee: Wiesmoor-Gartnerie und Baumschule GmbH, Fed. Rep. of Germany

[21] Appl. No.: 750,601

[22] Filed: Jul. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct Kalanchoe plant named Satisfaction, having bright pink flower color, compact habit with excellent self-branching, early flowering, and excellent flower keeping qualities.

1 Drawing Figure

The present invention relates to a new and distinctive cultivar of Kalanchoe plant, botanically known as *Kalanchoe blossfeldiana,* and referred to by the cultivar name Satisfaction.

Satisfaction was developed by me through controlled breeding by crossing Singapur (seed parent) with Asmara (pollen parent). Asexual reproduction of stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry:

1. Satisfaction is characterized by its compact habit, excellent self-branching, and early flowering habit.
2. The growth rate, self-branching, leaf size and thickness, early flowering, and flower quantity make Satisfaction ideal for 10 cm pot production.
3. Branching is similar to Sensation (disclosed in U.S. Plant Pat. No. 4,727), but not as good as Fascination (disclosed in a pending application of Applicant) or Singapur (disclosed in U.S. Plant Pat. No. 5,361).
4. Foliage is crenate with very shallow cuts like Singapur, while Sensation and Fascination have deeper crenate cuts. Leaves are rounded like Singapur and Fascination, while Sensation is more oblong.
5. After flower initiation, plants must be treated with Alar in all seasons to reduce peduncle elongation.
6. Flowering time is 9 weeks in summer and 12 weeks in winter from start of short days. Flowering is similar to Singapur and Fascination but earlier than Sensation, a 10 week cultivar in summer.
7. Flower color is a bright pink which is lighter than Fascination and much deeper than Sensation.
8. Flowers are larger than Singapur and similar in size to Fascination and Sensation. All noted cultivars have pointed tips on the petals.
9. Satisfaction is similar in height to Fascination and Sensation, but shorter than Singapur.

The accompanying colored photograph illustrates the overall appearance of this cultivar taken as a perspective view of the plant and showing the colors as true as it is reasonably possible to obtain in a colored reproduction of this type.

The following is a detailed description of my new Kalanchoe cultivar based on plants produced under commercial practices in the greenhouses of Wiesmoor Gartnerei in Wiesmoor, Germany. Color references are made to The Royal Horticultural Society Colour Chart except where general terms of ordinary dictionary significance are used.

Parentage: A controlled cross between Singapur and Asmara.

Propagation:

(A) *Type cutting.*—Short stem cutting up to 2 cm long.

(B) *Time to root.*—10 days at 21° C. summer. 14 days at 21° winter.

(C) *Rooting habit.*—Many fine fibrous roots.

Plant description:

(A) *Form.*—Short, compact, upright, best suited for growing and scheduling practices in 10 cm pots.

(B) *Habit of growth.*—Moderate rate of growth with excellent basal branching and branching from every node.

(C) *Foliage description.*—Leaves simple, opposite, dark green in color. (1) Size: Mature leaf on a plant grown in a 10 cm pot is 120 mm long and 70 mm. wide. (2) Shape: Ovate with obtuse apex and acute base. (3) Texture: Glabrous, coriaceous, succulent. (4) Margin: Crenate. (5) Color: Young foliage, top side 137B; under side 137C. Mature foliage, top side 147A; under side 147B.

Flowering description:

(A) *Flowering.*—Cyme inflorescence; each shoot is formed by dichotomous branching, starting with the opening of the terminal flower of the main axis, followed by terminal flowers of the side branching, continuing with subsequent development of branches in the inflorescence. Major inflorescence is 55 mm to 65 mm in diameter and lateral inflorescences are 40 mm to 50 mm in diameter.

(B) *Natural flowering season.*—Early January. Flowering time under controlled day length at 20° C. in summer is 9 weeks; in winter is 12 weeks. Flowering depends on temperature, light intensity, and other growing conditions.

(C) *Flower buds.*—Oblong, up to 7 mm long, developing to tubular as flower petals mature, sheathed with four light green sepals; corolla at maturity is 9 mm long.

(D) *Flowers borne.*—On compound dichasial cymes; peduncle is 3 mm in diameter, with peduncle length depending on growing conditions and Alar application; pedicels up to 12 mm long.

(E) *Quantity of flowers.*—Highly floriferous, main axis has over 100 flowers and lateral branches have over 75 flowers, with eight or more side branches in a 10 cm pot; long lasting.

(F) *Petals.*—(1) Shape: Nearly round, top cuspidate. (2) Color: Top when opening, near 52A, fading to near 54A; under side 54A. (3) Number and Size of Petals: Four, united in corolla; petals 6 mm in diameter; flower 14 mm in diameter.

(G) *Reproductive organs.*—(1) Stamens: Eight in number. (a) Anther shape: Flat, elliptical; yellow in color. (b) Filament color: Light green. (c) Pollen color: Yellow. (2) Pistels: (a) Stigma: Flat shape, greenish white immature to white mature. (b) Style color: Light green. (c) Ovaries: Four-celled, 7 mm, green in color.

Disease resistance: Resistant to mildew. No other disease problems to date.

I claim:

1. A new and distinct cultivar of Kalanchoe named Satisfaction, as described and illustrated, and particularly characterized by its bright pink flower color, compact habit with excellent self branching, early flowering, and excellent flower keeping qualities.

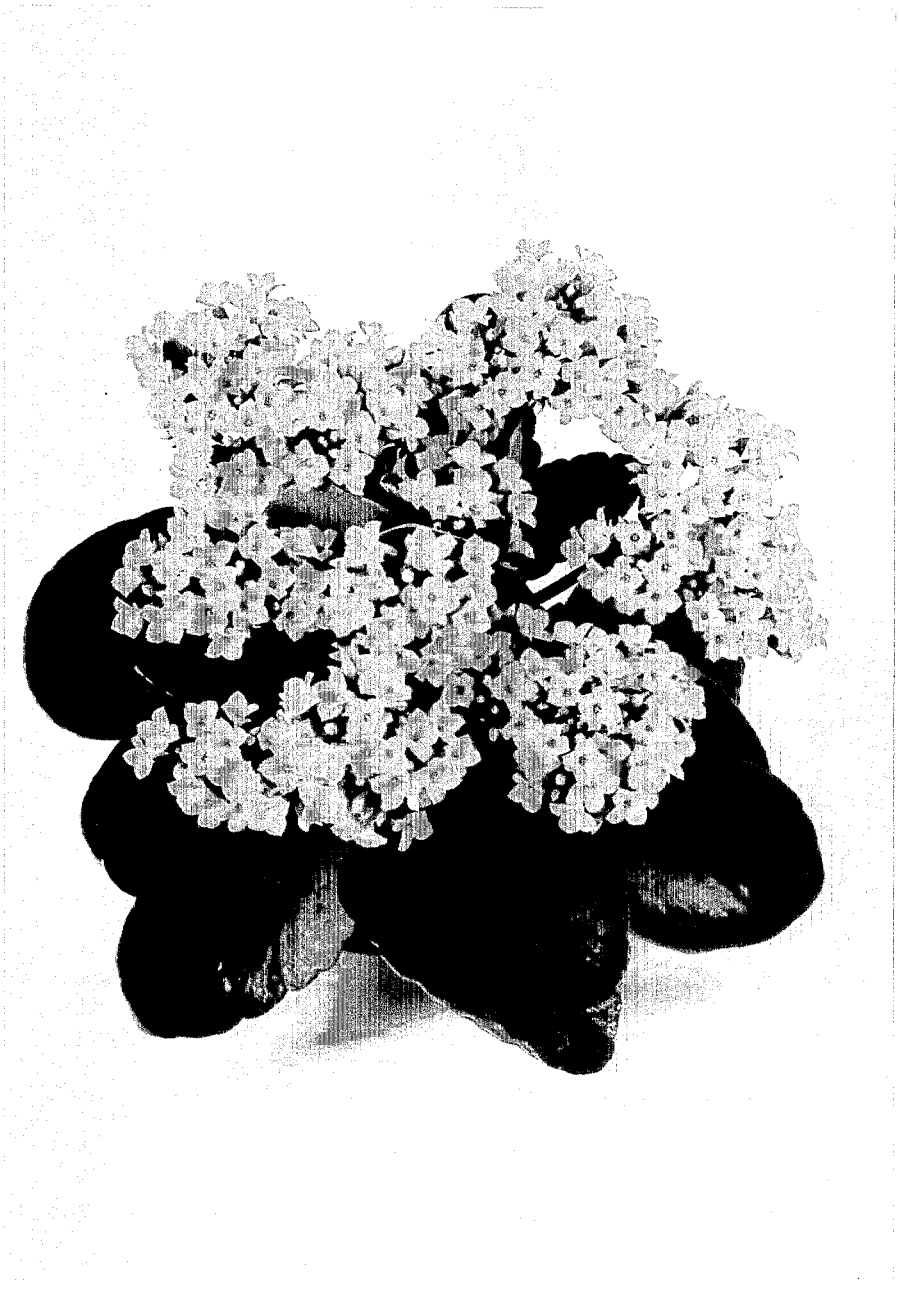

* * * * *